United States Patent [19]

Kuribayashi et al.

[11] Patent Number: 5,756,857
[45] Date of Patent: May 26, 1998

[54] CYCLOHEXANOL DERIVATIVE, COOL FEELING AND COOL FEELING COMPOSITION CONTAINING THE SAME, PROCESS FOR PRODUCING THE DERIVATIVE AND INTERMEDIATE THEREFOR

[75] Inventors: Mitsuru Kuribayashi; Mitsuru Tanoue; Akira Nakagawa; Munehiko Hirano; Hideshi Oda, all of Tosu, Japan

[73] Assignee: Hisamitsu Pharmaceutical Co., Inc., Tosu, Japan

[21] Appl. No.: 433,375

[22] PCT Filed: Oct. 28, 1993

[86] PCT No.: PCT/JP93/01562

§ 371 Date: Apr. 28, 1995

§ 102(e) Date: Apr. 28, 1995

[87] PCT Pub. No.: WO94/10117

PCT Pub. Date: May 11, 1994

[30] Foreign Application Priority Data

Oct. 29, 1992 [JP] Japan .................. 4-316438

[51] Int. Cl.$^6$ .................. C07C 41/00
[52] U.S. Cl. .................. 568/579; 568/670; 424/49; 424/55; 424/65; 424/69; 424/715; 514/715; 514/844; 514/847; 514/848; 514/901
[58] Field of Search .................. 568/579, 670; 424/49, 55, 65, 69, 715; 514/715, 844, 847, 848, 901

[56] References Cited

U.S. PATENT DOCUMENTS 2,656,385 10/1953 Hogg et al. .................. 568/579
4,654,167 3/1987 Degner et al. .................. 568/670 X
4,757,051 7/1988 Gramlich et al. .................. 568/579 X
4,956,341 9/1990 Degner et al. .................. 568/579 X
5,037,802 8/1991 Eilerman et al. .................. 568/670 X

FOREIGN PATENT DOCUMENTS 1315625 5/1973 United Kingdom .

Primary Examiner—Paul F. Shaver
Attorney, Agent, or Firm—Bucknam and Archer

[57] ABSTRACT

A cyclohexanol derivative represented by the following general formula (1) and preferably the following general formula (1a):

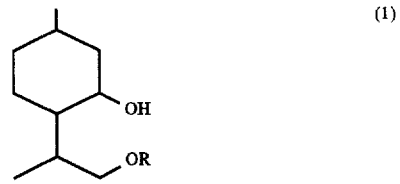

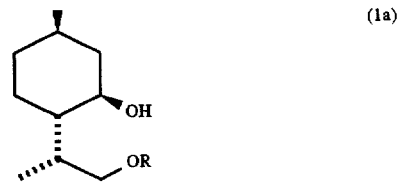

wherein R represents a linear or branched alkyl group having 1 to 5 carbon atoms. The above cyclohexanol derivative imparts satisfactory refrigeration to not only the mouth mucosa but also the skin. Moreover, it is practically odorless. A cool feeling and various cool feeling compositions which are practically odorless can be obtained from the cyclohexanol derivative.

7 Claims, No Drawings

CYCLOHEXANOL DERIVATIVE, COOL FEELING AND COOL FEELING COMPOSITION CONTAINING THE SAME, PROCESS FOR PRODUCING THE DERIVATIVE AND INTERMEDIATE THEREFOR

TECHNICAL FIELD

The present invention relates to a novel cyclohexanol derivative having refrigerating activity and to a cool feeling (refrigerant) and a cool feeling composition each containing the derivative. Moreover, the present invention relates to a process for producing the above cyclohexanol derivative and a novel benzyl cyclohexyl ether derivative being an intermediate therefor.

BACKGROUND ART

For long, peppermint oil and λ-menthol being a principal component thereof are known as substances each giving physiological cold flush to the skin and mouth mucosa, namely, having refrigerating activity. These are mixed as aromatics into foods, drinks, dentifrices, tobaccos and the like and are widely used in various cosmetics, external preparations and the like as refrigerants.

However, λ-menthol has had a drawback because, although it has satisfactory refrigerating activity, it is so crystalline that, when it is used in some composition forms, especially when it is mixed into a fomentation or a tape, it crystallizes in the base to thereby, for example, lower the release of other drugs with the result that a resolvent must be additionally added. Moreover, as is commonly known, λ-menthol has a powerful odor, so that it has been frequent that, when it is mixed into, for example, a cosmetic, the refined fragrance thereof is ruined.

Further, λ-menthol sublimes, so that its peculiar peppermint odor widely spreads even if its amount is very small and irritates the eyes and the mouth mucosa. Therefore, the work environment of a production process in which λ-menthol is handled has not been very favorable. Further, in recent years, there has been a problem that consumers tend to be nervous about the peppermint odor of drugs, etc., so that the use of λ-menthol is not favored. Still further, it has been difficult to persistently secure the stability of the quality of λ-menthol during use because λ-menthol sublimes.

In recent years, a number of patent applications have been filed relating to less odorous λ-menthol derivatives and homologues thereof. For example, Japanese Patent Laid-Open Nos. Gazette 16647/1972, 16649/1972, 88334/1983, 194049/1986 and 290827/1990 disclose menthol derivatives. Japanese Patent Laid-Open Gazette Nos. 93454/1983 and 95194/1983 tricyclic alcohols, and Japanese Patent Laid-Open Gazette No. 136544/1985 tricyclic amides as refrigerants. However, these are mostly far inferior to λ-menthol in the refrigeration intensity although their aromas are improved. Therefore, the conventional refrigerants other than λ-menthol have not been fully satisfactory in the application to the less sensitive skin or the like although they refrigerate a mouth mucosa believed to be highly sensitive to the refrigerants.

Consequently, the employment of the above λ-menthol and the conventional menthol homologues as ingredients of cosmetics and drugs has caused a problem in any of the refrigerating effect (1), the continuity of cool feeling function (2), the peculiar odor (peppermint odor) (3), the stability of the preparation (4) and the solubility (5), so that it has not led to offering a fully satisfactory product.

Thus, the object of the present invention is to develop a compound as well as a cool feeling and cool feeling composition both based on the compound, the compound having excellent properties, for example, having satisfactory refrigerating activity (1) being free from peppermint odor (2) not subliming at ordinary temperatures (3) not crystallizing in a base (4) and being highly compatible with various bases (5). The compound and cool feeling and cool feeling composition will be useful for developing various preparations such as cosmetics, buccals and drugs each intended for the mouth mucosa or the skin.

SUMMARY OF THE INVENTION

The inventors have made extensive and intensive studies with a view toward attaining the above objects. As a result, they have found that a novel cyclohexanol derivative represented by the structural formula shown hereinbelow has refrigerating activity equivalent to that of λ-menthol, is satisfactorily active to not only the mouth mucosa but also the skin and has advantageous properties, e.g., being practically odorless as compared with the odors of λ-menthol and peppermint oil. The present invention has been arrived at on the basis of the above finding.

Accordingly, the cyclohexanol derivative of the present invention is represented by the following general formula:

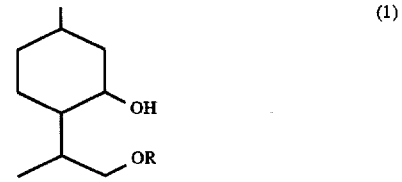

(1)

wherein R represents a linear or branched alkyl group having 1 to 5 carbon atoms.

The above cyclohexanol derivative of the present invention is a compound not described in any literature and first discovered by the inventors. The formal nomenclature thereof is 2-(2-alkoxy-1-methylethyl)-5-methylcyclohexanol. The above compound has a plurality of stereoisomers. Although any of them has strong refrigerating activity and is practically odorless, a cyclohexanol derivative represented by the following general formula:

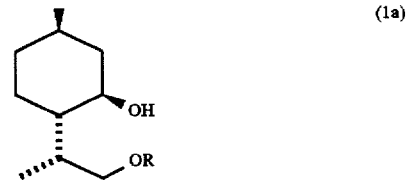

(1a)

wherein R represents a linear or branched alkyl group having 1 to 5 carbon atoms, namely (1R, 2S, 5R, 8R)-2-(2-alkoxy-1-menthyflethyl)-5-methylcyclohexanol is preferred from the viewpoint of, for example, the continuity of refrigeration.

Examples of the linear or branched alkyl groups each having 1 to 5 carbon atoms represented by R in the above general formulae (1) and (1a) include methyl, ethyl, n-propyl, isopropyl, n-butyl, isobutyl, sec-butyl, tert-butyl, n-pentyl, isopentyl, sec-pentyl, tert-pentyl and neopentyl groups. Of these, methyl, ethyl, isopropyl, tert-butyl and n-pentyl groups are preferred, and a methyl group is especially preferred.

The cool feeling and cool feeling composition of the present invention will now be described.

The cool feeling of the present invention contains the cyclohexanol derivative represented by the above general formula (1). In particular, the cool feeling of the present invention either may consist of only the above cyclohexanol derivative of the present invention because itself acts as a cool feeling or may be combined with other conventional refrigerants. Although, as the above cyclohexanol derivative, either any of the plurality of stereoisomers may be used individually or use may be made of a mixture thereof, it is preferred that the cyclohexanol derivative represented by the above general formula (1a) be employed individually.

As mentioned above, various applications of the cyclohexanol derivative of the present invention as providing a cool feeling may be found in, for example, drugs, quasidrugs, foods and cosmetics. Various cool feeling compositions each containing the above derivative can be obtained by the present invention. That is, the cool feeling composition of the present invention contains the cyclohexanol derivative represented by the above general formula (1).

Examples of the cool feeling compositions of the present invention include drugs such as ointments, creams, gels, lotions, shaping cataplasms, tapes and internal medicines (1), cosmetics such as powders, hair tonics, shampoos and lip colors (2), mouth washes such as dentifrices (3) and foods such as chewing gums, candies, ices and refreshing drinks (4), in which the above cyclohexanol derivative has been mixed as a cool feeling ingredient to impart refrigerating activity.

Other components of the cool feeling composition of the present invention are not particularly limited, and the cool feeling composition may be appropriately prepared by combining the cool feeling with conventional bases and drugs. An antiseptic, an antioxidant, a perfume, a colorant, a surfactant and other ingredients may be mixed in the cool feeling composition of the present invention as long as the mixing is not detrimental to the refrigerating activity of the above cyclohexanol derivative. When the cool feeling composition of the present invention is used as any of various preparations such as drugs and cosmetics, conventional drugs may be appropriately mixed therein as pharmaceutically active components.

Although the content of the above cyclohexanol derivative in the cool feeling composition of the present invention is not particularly limited, it is preferred that it be in the range of 0.001 to 10% by weight during use.

The cyclohexanol derivative of the present invention is excellent in all the above properties (1) to (5), so that all the refrigerants and cool feeling compositions each comprising the above derivative according to the present invention can satisfactorily refrigerate the skin or the like with practically no peppermint odor and are excellent in the continuity of the refrigerating activity and the immediate exertion of the activity.

The process for producing the above cyclohexanol derivative of the present invention will be described below. The cyclohexanol derivative of the present invention may be synthesized from, for example, isopulegol as a starting material according to the following reaction formula:

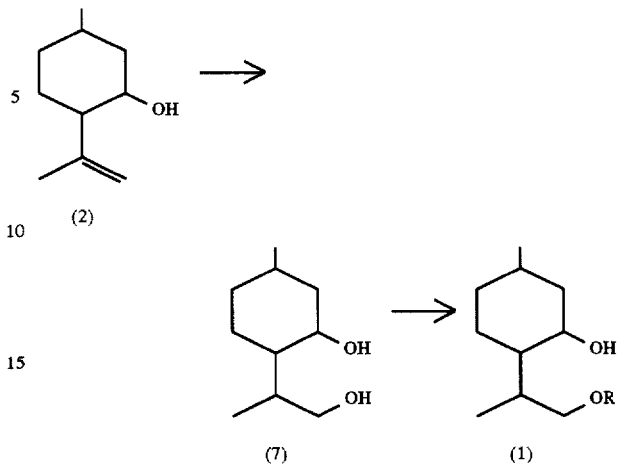

wherein R represents a linear or branched alkyl group having 1 to 5 carbon atoms.

Specifically, isopulegol (2) and sodium borohydride are dissolved in a solvent selected from among diethyl ether, tetrahydrofuran and diglyme. Boron trifluoride etherate is dropped into the solution to thereby obtain a mixture. Water is added to the mixture 1 to 2 hr later, and further aqueous solutions of sodium hydroxide and hydrogen peroxide are added. The resultant mixture is stirred well, and the obtained reaction product is extracted with, for example, ether. The solvent is distilled off, thereby obtaining a diol (7).

The diol (7) is dissolved in a solvent selected from among dimethylformamide, dimethyl sulfoxide, dimethoxyethane and tetrahydrofuran. A base selected from among sodium hydride, silver oxide, barium oxide, sodium hydroxide, triethylamine, potassium carbonate and sodium amide is added, and an equimolar amount of the corresponding alkyl halide is dropped. The reaction is conducted at a temperature of $-10°$ to $100°$ C. for a period of several to several tens of hours, thereby obtaining the desired cyclohexanol derivative (1).

The cyclohexanol derivative of the present invention may be obtained in the form of not only a mixture of some stereoisomers but also a pure specified stereoisomer by appropriately combining the above process with resolving means such as column separation and/or methods such as selection of starting materials.

However, the means such as column separation is quite time-consuming, so that it is not very favorable from the viewpoint of industrial application. Thus, the inventors established a novel process for selectively and effectively producing only the above (1R, 2S, 5R, 8R)-2-(2-alkoxy-1-methylethyl)-5-methylcyclohexanol represented by the general formula (1a) which is especially preferred among the cyclohexanol derivatives of the present invention.

That is, the inventors have made extensive and intensive studies with a view to providing an industrially advantageous process for synthesizing only the above cyclohexanol derivative represented by the general formula (1a). As a result, they have discovered that the above derivative can be produced in highly pure form, in a high yield and at a lowered cost by employing (–)-isopulegol as a starting compound and causing the same to pass through a specified reaction step.

The process of the present invention for producing the cyclohexanol derivative represented by the general formula (1a) will be described below.

The process of the present invention proceeds as shown hereinbelow:

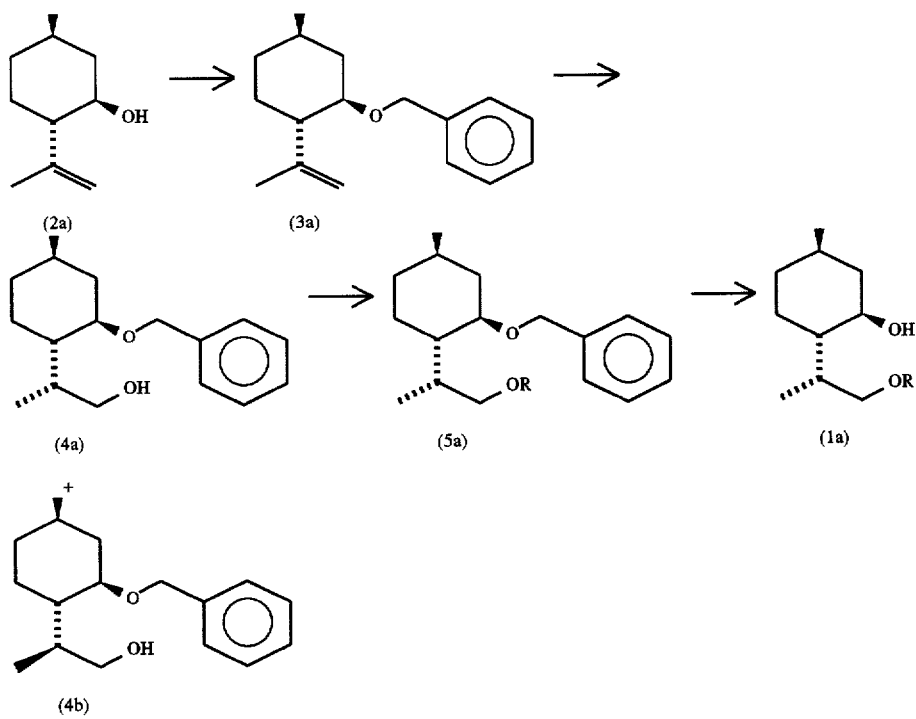

wherein R represents a linear or branched alkyl group having 1 to 5 carbon atoms.

Specifically, first, (−)-isopulegol (2a) is reacted with metallic sodium or sodium hydride in a benzenoid solvent such as toluene or xylene at a reflux temperature for 3 to 24 hr to thereby form a salt. While heating, a benzyl halide selected from among, for example, benzyl chloride and benzyl bromide is dropped into the mixture. After the completion of the dropping, the reflux temperature is held for 1 to 12 hr, and the reaction is terminated. The resultant reaction mixture is cooled, and water is added and agitated. The organic phase is separated, and the solvent is recovered. Vacuum distillation is conducted to thereby obtain a compound (3a). In the above reaction, the solvent is preferably used in an amount of about 1 to 10 times the weight of (−)-isopulegol. Each of the metallic sodium or sodium hydride and benzyl halide is preferably used in an amount of about 1 to twice the moles of (−)-isopulegol.

The obtained compound (3a) is converted to compounds (4a, 4b) through the hydroboration and hydrogen peroxide oxidation reaction conducted in various conditions which are commonly known by persons skilled in the art to which the present invention pertains. That is, the novel desired compounds (4a, b) can be obtained in a high yield by adding a B-H bond to the internal olefin of the compound (3a) with the use of a diborane (e.g., borane/THF complex or borane/ methyl sulfide complex, diisopynocamphenyl-borane, 9-borabicyclo[3.3.1]nonane (9-BBN) and dicyamylborane), followed by oxidation with hydrogen peroxide.

Preferably, the above diborane is generated by reacting sodium borohydride with a member selected from among various acids (e.g., boron trifluoride ether complex, aluminum chloride, sulfuric acid and dimethyl sulfate) in an organic solvent selected from among, for example, THF, diethyl ether and dimethoxyethane inside or outside the reaction system. Specifically, a diborane is generated by first dissolving the compound (3a) in a preferably 0.5 to 20-fold and still preferably 1 to 10-fold weight of an organic solvent (preferably tetrahydrofuran) and then employing sodium borohydride in an amount of preferably 1 to 1.5 times the moles of the compound (3a) together with an acid in an amount of preferably 1 to 1.5 times the moles of the sodium borohydride inside or outside the reaction system. Agitation is continued so as to prevent the temperature of the contents of the container from exceeding 40° C., and satisfactory agitation is conducted for 1 to 3 hr after the completion of the generation of the diborane. Subsequeantly, a 3M aqueous sodium hydroxide solution is added to the above reaction fluid in an amount of about 1 to 2 times the weight of the compound (3a), and further substantially the same amount of a 30% aqueous hydrogen peroxide solution is so gradually dropped in that the temperature of the contents of the container does not exceed 40° C. After the completion of the dropping, the reaction mixture is agitated at room temperature for 0.5 to 3 hr, and the organic phase is separated. Further, the reaction product is extracted from the water phase with the use of tetrahydrofuran and added to the previously separated organic phase. The organic phase is dried, and the solvent is distilled off. Thus, a mixture of a crystalline compound (4a) and a liquid compound (4b) is obtained.

In the above reaction, the compound (4a) is preferentially formed over the compound (4b) and the compound (4a) crystallizes while the compound (4b) is liquid, so that the compound (4a) can readily be isolated in pure form by washing with a solvent such as hexane in which the compound (4a) is insoluble.

The compound (4a) is converted to the compound (5a) by an alkylating agent such as a methylating agent in an organic solvent in the presence of a base. For example, N,N-dimethylformamide, dimethyl sulfoxide, tetrahydrofuran, dioxane or dimethoxyethane may be used as the organic solvent. The organic solvent is used in an amount of preferably about 1 to 20 times and still preferably about 2 to 10 times the weight of the compound (4a). Although sodium hydride or potassium tert-butoxide is especially preferred as the base, the type of the base is not limited as long as it can promote the alkylation. It is preferred that the alkylating agent be selected from among alkyl iodides, alkyl chlorides, alkyl bromides, dialkyl sulfates and the like and be used in an amount of about 1 to 2 mol per mol of the compound (4a). After the completion of the reaction, the reaction product is poured into water, neutralized and extracted with a suitable solvent. The resultant organic phase is washed with water, dried and concentrated, thereby obtaining a novel compound (5a) not described in any literature. If desired, the compound (5a) may be purified, for example, by vacuum distillation or through means such as column chromatography.

The reaction from the compound (5a) to the compound (1a) is effected by catalytic hydrogenetion (debenzylating reaction) of the compound (5a) conducted in a solvent selected from among ethanol, methanol, acetic acid, dioxane, cyclohexane and the like in the presence of a debenzylating agent such as palladium-carbon as a catalyst and in the presence of an acid such as sulfuric, hydrochloric, acetic or perchloric acid as a promoter. Thus, the cyclohexanol derivative of the present invention represented by the general formula (1a) is obtained. The solvent is used in an amount of preferably about 1 to 20 times and still preferably about 2 to 5 times the weight of the compound (5a). It is preferred that the acid concentration be in the range of 0.1 to 2N. When the acid concentration is below the lower limit, the reaction is likely not to proceed at a desirable rate. On the other hand, when the acid concentration exceeds the upper limit, side reactions other than the desired reaction are likely to occur. The debenzylating agent is preferably used in an amount of 1 to 10% by weight based on the compound (5a). Although the above reaction may be effected under atmospheric pressure, it is preferred that the reaction be carried out under a pressure of 2 to 5 kg/cm$^2$.

In the production of the cyclohexanol derivative of the present invention represented by the general formula (1a) according to the above process of the present invention, the inventors have found that the above compounds represented by the general formulae (4a) and (5a) are novel compounds useful as intermediates. Therefore, the present invention also relates to the intermediates for producing the cyclohexanol derivative. The novel benzyl cyclohexyl ether derivative of the present invention will be described below.

The benzyl cyclohexyl ether derivative of the present invention is represented by the following general formula:

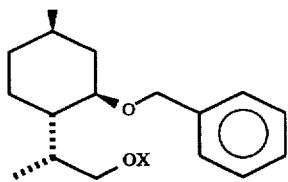

(6a)

wherein X represents H or a linear or branched alkyl group having 1 to 5 carbon atoms. In the above general formula (6a), X is either a hydrogen atom or the same alkyl group as with respect to the above R of the general formula (1). When X is a hydrogen atom, the above compound corresponds to the compound (4a) mentioned hereinbefore. On the other hand, when X is an alkyl group, the above compound corresponds to the compound (5a) mentioned hereinbefore. As mentioned above, the benzyl cyclohexyl ether derivative of the present invention is extremely useful as an intermediate for effectively producing on an industrial scale the cyclohexanol derivative of the present invention represented by the general formula (1a).

BEST MODE FOR CARRYING OUT THE INVENTION

The present invention will be illustrated in greater detail with reference to the following Examples, etc., which should not be construed as limiting the invention.

Referential Example 1

Synthesis of (1R, 2S, 5R)-2-(2-hydroxy-1-methylethyl)-5-methylcyclohexanol 5.1 g (0.13 mol) of sodium borohydride, 700 ml of diglyme and 50.0 g (0.32 mol) of (−)-isopulegol were charged into a 1λ three-necked flask equipped with a condenser, a dropping funnel, a thermometer and a magnetic stirrer. 23.0 ml (0.13 mol) of boron trifluoride etherate was put in the flask on a water bath, and the contents thereof were agitated well for 15 min (precipitated). Further, the contents were agitated at room temperature for 1 hr, and then 50 ml of water was added to thereby decompose any excess hydroxide. 40 ml of a 3M aqueous sodium hydroxide solution was added to the organic borane formed by the above reaction on the water bath heated at 30° to 50° C. Further, 40 ml of a 30% aqueous hydrogen peroxide solution was added and agitated well for 30 mins. The reaction product was extracted with 1λ of ether and washed with the same amount of chilled water 5 times to thereby remove the diglyme. The resultant ether phase was dried over anhydrous magnesium sulfate, and the solvent was distilled off, thereby obtaining 45.0 g (yield: 80.8%) of (1R, 2S, 5R)-2-(2-hydroxy-1-methylethyl)-5-methylcyclohexanol in the form of white crystals (reference: Helv. Chim. Acta., 50(21), 153 (1967)).

Referential Example 2

Isolation of (1R, 2S, 5R, 8R)-2-(2-hydroxy-1-methylethyl)-5-methylcyclohexanol

For 30.0 g of the compound obtained in Referential Example 1, a column separation was conducted using a solution of a 1:1 mixture of chloroform and ethyl acetate and the solvent was distilled off. Thus, 24.7 g (yield: 82.3%) of (1R, 2S, 5R, 8R)-2-(2-hydroxy-1-methylethyl)-5-methylcyclohexanol was obtained in the form of white crystals.

Example 1

Synthesis of (1R, 2S, 5R)-2-(2-methoxy-1-methylethyl)-5-methylcyclohexanol 20.0 g (0.12 mol) of (1R, 2S, 5R)-2-(2-hydroxy-1-methylethyl)-5-methylcyclohexanol obtained in Referential Example 1 was dissolved in 100 ml of dimethylformamide, and 3.3 g (0.14 mol) of sodium hydride was added to the solution. The mixture was agitated for 30 min, and 19.8 g (0.14 mol) of methyl iodide was dropped thereinto and continued to agitate at room temperature for 24 hr. After the completion of the reaction, 300 ml of water was added to the reaction solution and agitated. The reaction product was extracted with ether. The resultant ether phase was dried over anhydrous magnesium sulfate, and the solvent was distilled off, thereby obtaining 19.5 g (yield: 87.4%) of (1R, 2S, 5R)-2-(2-methoxy-1-methylethyl)-5-methylcyclohexanol in the form of a colorless liquid. The mass spectrometry and NMR data of the obtained compound are as follows:

MS (M/e): 187 (M+1),

NMR (CDCl$_3$, ppm):
 0.84–1.01 (8H; 3-Hax, 4-Hax, 7-CH$_3$, 9-CH$_3$),
 1.09–1.68 (5H; 2-H, 3-Heq, 4-Heq, 5-H, 6-Hax),
 1.92–2.06 (2H; 6-Heq, 8-H), and
 3.26–3.71 (6H; 1-H, —OCH$_2$—, —OCH$_3$).

Example 2
Isolation of (1R, 2S, 5R, 8R)-2-(2-methoxy-1-methylethyl)-5-methylcyclohexanol For 18.0 g of the compound obtained in Example 1, a column separation was conducted using a 1:1:2 mixture of ethyl acetate, chloroform and hexane and the solvent was distilled off. Thus, 14.3 g (yield: 79.7%) of (1R, 2S, 5R, 8R)-2-(2-methoxy-1-methylethyl)-5-methylcyclohexanol was obtained in the form of a colorless liquid. The stereostructural formula, mass spectrometry data and NMR data of the obtained compound are as follows:

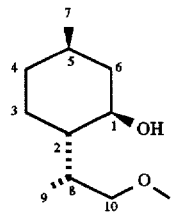

MS (M/e): 187 (M+1),
NMR (CDCl$_3$, ppm):
  0.80–1.01 (8H; 7-CH$_3$, 9-CH$_3$, 3-Hax, 4-Hax),
  1.07–1.69 (5H; 2-H, 3-Heq, 4-Heq, 5-H, 6-Hax),
  1.92–2.04 (2H; 8-H, 6-Heq),
  3.27–3.45 (6H; —OCH$_2$—, —OCH$_3$, 1-H), and
  3.72 (1H; —OH).

Example 3
Synthesis of (1R, 2S, 5R, 8R)-2-(2-methoxy-1-methylethyl)-5-methylcyclohexanol The same procedure as in Example 1 was repeated except that 20.0 g of (1R, 2S, 5R, 8R)-2-(2-hydroxy-1-methylethyl)-5-methylcyclohexanol was employed as the starting compound. Thus, 19.6 g (yield: 90.5%) of (1R, 2S, 5R, 8R)-2-(2-methoxy-1-methylethyl)-5-methylcyclohexanol was obtained in the form of a colorless liquid. The obtained compound was identical with that obtained in Example 2.

Example 4
Synthesis of (1R, 2S, 5R)-2-(2-ethoxy-1-methylethyl)-5-methylcyclohexanol 20.0 g (0.12 mol) of (1R, 2S, 5R)-2-(2-hydroxy-1-methylethyl)-5-methylcyclohexanol was dissolved in 100 ml of dimethylformamide, and 3.3 g (0.14 mol) of sodium hydride was added to the solution. The mixture was agitated for 30 min, and 21.8 g (0.14 mol) of ethyl iodide was dropped thereinto and continued to agitate at room temperature for 24 hr. After the completion of the reaction, 300 ml of water was added to the reaction fluid and agitated. The reaction product was extracted with ether. The resultant ether phase was dried over anhydrous magnesium sulfate, and the solvent was distilled off, thereby obtaining 20.1 g (yield: 86.4%) of (1R, 2S, 5R)-2-(2-ethoxy-1-methyl-ethyl)-5-methylcyclohexanol in the form of a colorless liquid. The mass spectrometry and NMR data of the obtained compound are as follows:

MS (M/e): 201 (M+1),
NMR (CDCl$_3$, ppm):
  0.81–1.03 (8H; 3-Hax, 4-Hax, 7-CH$_3$, 9-CH$_3$),
  1.11–1.69 (8H; 2-H, 3-Heq, 4-Heq, 5-H, 6-Hax, —OCH$_2$CH$_3$),
  1.90–2.03 (2H; 6-Heq, 8-H), and
  3.23–3.68 (5H; 1-H, —OCH$_2$CH—, —OCH$_2$CH$_3$).

Example 5
Isolation of (1R, 2S, 5R, 8R)-2-(2-ethoxy-1-methylethyl)-5-methylcyclohexanol For 18.0 g of the compound obtained in Example 3, column separation was conducted using a 1:1:2 mixture of ethyl acetate, chloroform and hexane and the solvent was distilled off. Thus, 14.9 g (yield: 82.7%) of (1R, 2S, 5R, 8R)-2-(2-ethoxy-1-methylethyl)-5-methylcyclohexanol was obtained in the form of a colorless liquid. The stereostructural formula, mass spectrometry data and NMR data of the obtained compound are as follows:

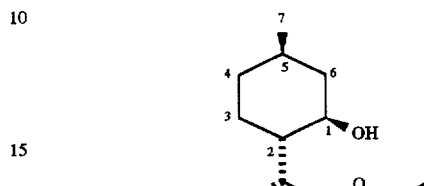

MS (M/e): 201 (M+1),
NMR (CDCl$_3$, ppm):
  0.80–1.01 (8H; 7-CH$_3$, 9-CH$_3$, 3-Hax, 4-Hax),
  1.10–1.68 (8H; 2-H, 3-Heq, 4-Heq, 5-H, 6-Hax, —OCH$_2$CH$_3$),
  1.89–2.03 (2H; 6-Heq, 8-H),
  3.32–3.55 (5H; 1-H, —OCH$_2$—, —OCH$_2$CH$_3$), and
  4.14 (1H; —OH).

Example 6
Synthesis of (1R, 2S, 5R)-2-(2-isopropoxy-1-methylethyl)-5-methylcyclohexanol 20.0 g (0.12 mol) of (1R, 2S, 5R)-2-(2-hydroxy-1-methylethyl)-5-methylcyclohexanol was dissolved in 100 ml of dimethoxyethane, and 3.3 g (0.14 mol) of sodium hydride was added to the solution. The mixture was agitated for 30 min, and 23.7 g (0.14 mol) of isopropyl iodide was dropped thereinto and continued to agitate at room temperature for 24 hr. After the completion of the reaction, 300 ml of water was added to the reaction fluid and agitated. The reaction product was extracted with ether. The resultant ether phase was dried over anhydrous magnesium sulfate, and the solvent was distilled off, thereby obtaining 18.3 g (yield: 73.6%) of (1R, 2S, 5R)-2-(2-isopropoxy-1-methylethyl)-5-methylcyclohexanol in the form of a colorless liquid. The mass spectrometry and NMR data of the obtained compound are as follows:

MS (M/e): 215 (M+1),
NMR (CDCl$_3$, ppm):
  0.85–1.05 (8H; 3-Hax, 4-Hax, 7-CH$_3$, 9-CH$_3$),
  1.13–1.70 (11H; 2-H, 3-Heq, 4-Heq, 5-H, 6-Hax, —OCH(CH$_3$)$_2$),
  1.95–2.11 (2H; 6-Heq, 8-H), and
  3.19–3.75 (4H; 1-H, —OCH$_2$—, —OCH(CH$_3$)$_2$).

Example 7
Isolation of (1R, 2S, 5R, 8R)-2-(2-isopropoxy-1-methylethyl)-5-methylcyclohexanol For 15.0 g of the compound obtained in Example 5, a column separation was conducted using a 1:1:2 mixture of ethyl acetate, chloroform and hexane and the solvent was distilled off. Thus, 12.5 g (yield: 83.1%) of (1R, 2S, 5R, 8R)-2-(2-isopropoxy-1-methylethyl)-5-methylcyclohexanol was obtained in the form of a colorless liquid. The stereostructural formula, mass spectrometry data and NMR data of the obtained compound are as follows:

11

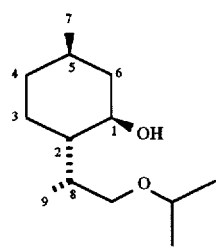

MS (M/e): 215 (M+1).

NMR (CDCl$_3$, ppm)
 0.80–1.03 (8H; 7-CH$_3$, 9-CH$_3$, 3-Hax, 4-Hax),
 1.11–1.68 (11H; —OCH(CH$_3$)$_2$, 2-H, 3-Heq, 4-Heq, 5-H, 6-Hax),
 1.85–2.02 (2H; 6-Heq, 8-H),
 3.33–3.65 (4H; 1-H, —OCH$_2$—, —OCH(CH$_3$)$_2$),
 and 4.39 (1H; —OH).

Referential Example 3
Synthesis of benzyl (1R, 2S, 5R)-2-isopropenyl-5-methyl cyclohexyl ether (compound (3a))

230 ml of toluene, 77.0 g (0.5 mol) of (−)-isopulegol and 12.7 g (0.55 mol) of metallic sodium were mixed together and heated. The mixture was held at reflux temperature for 18 hr to thereby form a salt. Then, 82.3 g (0.65 mol) of benzyl chloride was dropped into the mixture over a period of 1 hr and held at reflux temperature for 2 hr to effect a reaction. The container and the contents thereof were cooled, and 300 ml of water was added. The resultant organic phase was separated, washed with a saline solution and dried over anhydrous magnesium sulfate. Thereafter, the toluene was recovered, and vacuum distillation was conducted to thereby obtain 108.6 g (yield: 89%) of the compound (3a). The stereostructural formula, boiling point, mass spectrometry data and NMR data of the obtained compound are as follows:

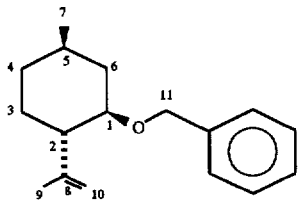

b.p.=118°–121° C./3 mmHg,
MS (M/e): 244 (M+),
NMR (CDCl$_3$, ppm)
 0.82–1.05 (5H; 3-Hax, 4-Hax, 7-CH$_3$),
 1.21–1.71 (7H; 9-CH$_3$, 3-Heq, 4-Heq, 5-H, 6-Hax),
 2.02–2.21 (2H; 2-H, 6-Heq),
 3.22–3.35 (1H; 1-H),
 4.39–4.82 (4H; —OCH$_2$C$_6$H$_5$, C=CH$_2$); and
 7.18–7.35 (5H; benzene ring).

Example 8
Synthesis of benzyl (1R, 2S, 5R, 8R)-2-(2-hydroxy-1-methylethyl)-5-methylcyclohexyl ether (compound (4a))

61 g (0.25 mol) of the compound (3a) obtained in Referential Example 3 and 9.5 g (0.25 mol) of sodium borohydride were dissolved in 100 ml of anhydrous THF. 31.5 g (0.25 mol) of dimethyl sulfate was dropped into the solution while holding the internal temperature at 40° C. or below and agitated at room temperature for 2 hr. Thereafter, the reaction solution was cooled with ice, and 100 ml of water was carefully dropped thereinto. After the completion of the dropping, 100 ml of a 3M aqueous NaOH solution was dropped into the reaction solution and further 100 ml of a 30% aqueous hydrogen peroxide solution was added while holding the internal temperature at 40° C. or below. The mixture was agitated for 30 min, and the organic phase was separated. The reaction product was extracted from the water phase with 500 ml of n-hexane and added to the organic phase. The organic phase was washed with water and a saturated saline solution and dried over anhydrous magnesium sulfate. Thereafter, the solvent was distilled off, and the resultant crystals were washed with n-hexane to thereby obtain 47.8 g (yield: 73%) of the compound (4a). The stereostructural formula, melting point, mass spectrometry data and NMR data of the obtained compound are as follows:

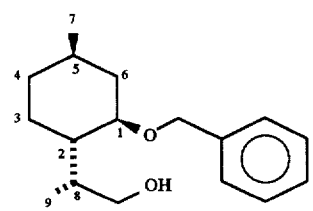

m.p.=82.5°–83.5° C.,
MS (M/e): 262 (M+),
 0.82–0.99 (8H; 3-Hax, 4-Hax, 7-CH$_3$, 9-CH$_3$),
 1.12–1.94 (6H; 2-H, 3-Heq, 4-Heq, 5-H, 6-Hax, 8-H),
 2.24 (1H; 6-Heq),
 2.59 (1H; —OH),
 3.22–3.54 (3H; 1-H, —OCH$_2$OH),
 4.36–4.70 (2H; —OCH$_2$C$_6$H$_5$), and
 7.24–7.36 (5H; benzene ring).

Example 9

Synthesis of benzyl (1R, 2S, 5R, 8R)-2-(2-methoxy-1-methylethyl)-5-methylcyclohexyl ether (compound (5a))

80 ml of a DMF solution containing 40 g (153 mmol) of the compound (4a) obtained in Example 8 was dropped into 40 ml of a DMF solution containing 9.2 g of sodium hydride (230 mmol, 60% in oil) while cooling with ice. After the completion of the dropping, the reaction fluid was agitated for 1 hr, and 32.6 g (230 mmol) of methyl iodide was dropped thereinto while cooling with ice over a period of 30 min. The reaction fluid was agitated at room temperature for 3 hr and carefully poured into ice water, and the reaction product was extracted with hexane. The organic phase was separated, washed with a saline solution and dried over anhydrous magnesium sulfate. The solvent was recovered, and the resultant residue was distilled at a reduced pressure, thereby obtaining 42.1 g (yield: 90%) of the compound (5a). The stereostructural formula, boiling point, mass spectrometry data and NMR data of the obtained compound are as follows:

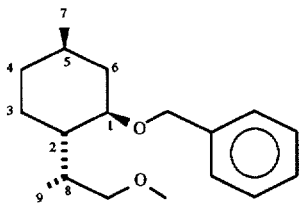

b.p.=188°–191° C./3 mmHg,
MS (M/e): 276 (M+),
NMR (CDCl$_3$, ppm)
0.79–1.72 (13H; 2-H, 3-Hax, 3-Heq, 4-Hax, 4-Heq, 5-H, 6-Hax, 7-CH$_3$, 9-CH$_3$),
2.13–2.32 (2H; 6-Heq, 8-H),
3.13–3.36 (6H; 1-H, —CH$_2$OCH$_3$, —OCH$_3$),
4.38–4.68 (2H; —OCH$_2$C$_6$H$_5$), and
7.21–7.37 (5H; benzene ring).

Example 10
Synthesis of (1R, 2S, 5R, 8R)-2-(2-methoxy-1-methyl ethyl)-5-methylcyclohexanol (compound (1a))

45.0 g (163 mmol of the compound (5a) obtained in Example 9 was dissolved in 120 ml of a 1N hydrochloric acid/ethanol mixture in a pressure glass, and 2.25 g (5% by weight) of 5%-palladium-carbon was carefully added to the solution. The inside of the reaction vessel was pressurized to 3 kg/cm$_2$ with hydrogen gas, and the mixture was agitated at room temperature. While confirming the absorption of hydrogen, 3 hr later, the internal pressure of the reaction vessel was released to atmospheric pressure to thereby terminate the reaction. The catalyst was filtered off, the the solvent evaporated, and the reaction product extracted with 500 ml of ether. The extract was washed with 500 ml of a 1N aqueous sodium hydroxide solution, and the ether was distilled therefrom. Vacuum distillation was conducted, thereby obtaining 27.9 g (yield: 92.0%) of (1R, 2S, 5R, 8R)-2-(2-methoxy-1-methylethyl)-5-methylcyclohexanol (compound (1a)).

| Formulation Example 1 lotion | |
|---|---|
| | (% by weight) |
| ethanol | 59.0 |
| purified water | 35.0 |
| propylene glycol | 5.0 |
| (1R, 2S, 5R)-2-(2-methoxy-1-methyl-ethyl)-5-methylcyclohexanol | 1.0 |

The lotion of the above formulation was prepared and applied to the skin. The application imparted the same refreshing refrigeration as induced by menthol to the skin.

| Formulation Example 2 hair tonic | |
|---|---|
| | (% by weight) |
| ethanol | 52.0 |
| jojoba oil | 0.4 |
| polyoxyethylene sorbitan laurate | 1.2 |
| propylene glycol | 1.2 |
| triclosan | 0.1 |
| coloring matter | trace |

| Formulation Example 2 hair tonic | |
|---|---|
| | (% by weight) |
| (1R, 2S, 5R)-2-(2-methoxy-1-methylethyl)-5-methylcyclohexanol | 0.5 |
| purified water | balance |

The above components were mixed together and homogenized, thereby obtaining a hair tonic. When the hair tonic was applied to the scalp, refreshing refrigeration remained even after the termination of the cooling effect exerted by the evaporation of ethanol.

| Formulation Example 3 skin lotion | |
|---|---|
| | (% by weight) |
| ethanol | 20.0 |
| propylene glycol | 5.0 |
| glycerol | 4.5 |
| methyl p-hydroxybenzoate | 0.1 |
| perfume | 0.2 |
| purified water | 70.0 |
| (1R, 2S, 5R)-2-(2-ethoxy-1-methylethyl)-5-methylcyclohexanol | 0.2 |

The above components were mixed together, thereby obtaining a skin lotion. The application thereof to the skin caused no irritancy and imparted refreshing refrigeration to the skin.

| Formulation Example 4 dentifrice | |
|---|---|
| | (% by weight) |
| calcium hydrogenphosphate | 50.0 |
| carboxymethylcellulose | 1.0 |
| sodium lauryl sulfate | 2.0 |
| glycerol | 25.0 |
| saccharin | 0.2 |
| perfume | 0.8 |
| (1R, 2S, 5R)-2-(2-methoxy-1-methylethyl)-5-methylcyclohexanol | 0.1 |
| purified water | balance |

The above components were mixed together, thereby obtaining a dentifrice. Upon the use thereof, refreshing refrigeration spread in the mouth.

| Formulation Example 5 shampoo | |
|---|---|
| | (% by weight) |
| sodium lauryl sulfate | 12.0 |
| purified water | 87.5 |
| (1R, 2S, 5R)-2-(2-methoxy-1-methylethyl)-5-methylcyclohexanol | 0.5 |

The above components were agitated and dispersed to thereby obtain a shampoo. Upon the use thereof, refreshing refrigeration remained on the scalp even after the use.

| Formulation Example 6 cream | |
|---|---|
| | (% by weight) |
| liquid paraffin | 10.0 |
| triglyceride of middle-length-chain fatty acid | 5.0 |
| polyethylene glycol monostearate | 3.0 |
| glycerol | 5.0 |
| carboxyvinylpolymer | 1.0 |
| diisopropanolamine | 0.4 |
| methyl p-hydroxybenzoate | 0.2 |
| (1R, 2S, 5R)-2-(2-methoxy-1-methylethyl)-5-methylcyclohexanol | 2.0 |
| purified water | balance |

The above components were mixed together, thereby obtaining a cream. Upon the application thereof to the skin, refreshing refrigeration remained on the skin.

| Formulation Example 7 ointment | |
|---|---|
| | (% by weight) |
| white petrolatum | 76.0 |
| glycerol monostearate | 10.0 |
| beef tallow | 10.0 |
| silicone oil | 1.0 |
| (1R, 2S, 5R)-2-(2-methoxy-1-methylethyl)-5-methylcyclohexanol | 3.0 |

The above components were agitated and mixed together, thereby obtaining an ointment. The application thereof to the skin imparted the same refrigeration as induced by menthol.

| Formulation Example 8 cataplasm | |
|---|---|
| | (% by weight) |
| gelatin | 5.0 |
| sorbitol | 10.0 |
| carboxymethylcellulose | 3.5 |
| glycerol | 25.0 |
| kaolin | 7.0 |
| sodium polyacrylate | 3.0 |
| (1R, 2S, 5R)-2-(2-methoxy-1-methylethyl)-5-methylcyclohexanol | 0.5 |
| purified water | 46.0 |

The above components were heated and mixed together to thereby obtain a paste. The paste was spread on a foundation, thereby obtaining a cataplasm. This imparted the same refrigeration as induced by menthol to the skin.

| Formulation Example 9 cataplasm | |
|---|---|
| | (% by weight) |
| gelatin | 6.0 |
| polyvinyl alcohol | 3.5 |
| copolymer of methoxyethylene and maleic anhydride | 2.5 |
| glycerol | 30.0 |
| kaolin | 5.0 |
| sodium polyacrylate | 2.0 |

| Formulation Example 9 cataplasm | |
|---|---|
| | (% by weight) |
| (1R, 2S, 5R)-2-(2-isopropoxy-1-methylethyl)-5-methylcyclohexanol | 0.5 |
| purified water | 50.5 |

The above components were heated and mixed together to thereby obtain a paste. The paste was spread on a foundation, thereby obtaining a cataplasm. This imparted the same refrigeration as induced by menthol to the skin.

| Formulation Example 10 lotion | |
|---|---|
| | (% by weight) |
| ethanol | 59.0 |
| purified water | 35.0 |
| propylene glycol | 5.0 |
| (1R, 2S, 5R, 8R)-2-(2-methoxy-1-methylethyl)-5-methylcyclohexanol | 1.0 |

The lotion of the above formulation was prepared and applied to the skin. The application imparted the same refreshing refrigeration as induced by menthol to the skin.

| Formulation Example 11 hair tonic | |
|---|---|
| | (% by weight) |
| ethanol | 52.0 |
| jojoba oil | 0.4 |
| polyoxyethylene sorbitan laurate | 1.2 |
| propylene glycol | 1.2 |
| triclosan | 0.1 |
| coloring matter | trace |
| (1R, 2S, 5R, 8R)-2-(2-methoxy-1-methylethyl)-5-methylcyclohexanol | 0.5 |
| purified water | balance |

The above components were mixed together and homogenized, thereby obtaining a hair tonic. When the hair tonic was applied to the scalp, refreshing refrigeration remained even after the termination of the cooling effect exerted by the evaporation of ethanol.

| Formulation Example 12 skin lotion | |
|---|---|
| | (% by weight) |
| ethanol | 20.0 |
| propylene glycol | 5.0 |
| glycerol | 4.5 |
| methyl p-hydroxybenzoate | 0.1 |
| perfume | 0.2 |
| purified water | 70.0 |
| (1R, 2S, 5R, 8R)-2-(2-methoxy-1-methylethyl)-5-methylcyclohexanol | 0.2 |

The above components were mixed together, thereby obtaining a skin lotion. The application thereof to the skin caused no irritancy and imparted refreshing refrigeration to the skin.

| Formulation Example 13 dentifrice | |
|---|---|
| | (% by weight) |
| calcium hydrogenphosphate | 50.0 |
| carboxymethylcellulose | 1.0 |
| sodium lauryl sulfate | 2.0 |
| glycerol | 25.0 |
| saccharin | 0.2 |
| perfume | 0.8 |
| (1R, 2S, 5R, 8R)-2-(2-methoxy-1-methyl-ethyl)-5-methylcyclohexanol | 0.1 |
| purified water | balance |

The above components were mixed together, thereby obtaining a dentifrice. Upon the use thereof, refreshing refrigeration spread in the mouth.

| Formulation Example 14 shampoo | |
|---|---|
| | (% by weight) |
| sodium lauryl sulfate | 12.0 |
| purified water | 87.5 |
| (1R, 2S, 5R, 8R)-2-(2-methoxy-1-methyl-ethyl)-5-methylcyclohexanol | 0.5 |

The above components were agitated and dispersed to thereby obtain a shampoo. Upon the use thereof, refreshing refrigeration remained on the scalp even after the use.

| Formulation Example 15 cream | |
|---|---|
| | (% by weight) |
| liquid paraffin | 10.0 |
| triglyceride of middle-length-chain fatty acid | 5.0 |
| polyethylene glycol monostearate | 3.0 |
| glycerol | 5.0 |
| carboxyvinylpolymer | 1.0 |
| diisopropanolamine | 0.4 |
| methyl p-hydroxybenzoate | 0.2 |
| (1R, 2S, 5R, 8R)-2-(2-methoxy-1-methyl-ethyl)-5-methylcyclohexanol | 2.0 |
| purified water | balance |

The above components were mixed together, thereby obtaining a cream. Upon the application thereof to the skin, refreshing refrigeration remained on the skin.

| Formulation Example 16 ointment | |
|---|---|
| | (% by weight) |
| white petrolatum | 76.0 |
| glycerol monostearate | 10.0 |
| beef tallow | 10.0 |
| silicone oil | 1.0 |
| (1R, 2S, 5R, 8R)-2-(2-methoxy-1-methyl-ethyl)-5-methylcyclohexanol | 3.0 |

The above components were agitated and mixed together, thereby obtaining an ointment. The application thereof to the skin imparted the same refrigeration as induced by menthol.

| Formulation Example 17 cataplasm | |
|---|---|
| | (% by weight) |
| gelatin | 5.0 |
| sorbitol | 10.0 |
| carboxymethylcellulose | 3.5 |
| glycerol | 25.0 |
| kaolin | 7.0 |
| sodium polyacrylate | 3.0 |
| (1R, 2S, 5R, 8R)-2-(2-methoxy-1-methyl-ethyl)-5-methylcyclohexanol | 0.5 |
| purified water | 46.0 |

The above components were heated and mixed together to thereby obtain a paste. The paste was spread on a foundation, thereby obtaining a cataplasm. This imparted the same refrigeration as induced by menthol to the skin.

| Formulation Example 18 cataplasm | |
|---|---|
| | (% by weight) |
| gelatin | 6.0 |
| polyvinyl alcohol | 3.5 |
| copolymer of methoxyethylene and maleic anhydride | 2.5 |
| glycerol | 30.0 |
| kaolin | 5.0 |
| sodium polyacrylate | 2.0 |
| (1R, 2S, 5R, 8R)-2-(2-isopropoxy-1-methyl-ethyl)-5-methylcyclohexanol | 0.5 |
| purified water | 50.5 |

The above components were heated and mixed together to thereby obtain a paste. The paste was spread on a foundation, thereby obtaining a cataplasm. This imparted the same refrigeration as induced by menthol to the skin.

| Formulation Example 19 cataplasm | |
|---|---|
| | (% by weight) |
| gelatin | 6.0 |
| polyvinyl alcohol | 3.5 |
| copolymer of methoxyethylene and maleic anhydride | 2.5 |
| glycerol | 30.0 |
| kaolin | 5.0 |
| sodium polyacrylate | 2.0 |
| (1R, 2S, 5R, 8R)-2-(2-ethoxy-1-methyl-ethyl)-5-methylcyclohexanol | 0.5 |
| purified water | 50.5 |

The above components were heated and mixed together to thereby obtain a paste. The paste was spread on a foundation, thereby obtaining a cataplasm. This imparted the same refrigeration as induced by menthol to the skin.

| Comparative Example 1 cataplasm | |
|---|---|
| | (% by weight) |
| gelatin | 5.0 |
| sorbitol | 10.0 |
| carboxymethylcellulose | 3.5 |

Comparative Example 1 cataplasm

| | (% by weight) |
|---|---|
| glycerol | 25.0 |
| kaolin | 7.0 |
| sodium polyacrylate | 3.0 |
| l-menthol | 0.5 |
| crotamiton | 1.0 |
| purified water | 45.0 |

The above components were heated and mixed together to thereby obtain a paste. The paste was spread on a foundation, thereby obtaining a cataplasm. Crotamiton was used as a resolvent for λ-menthol in this Comparative Example.

Comparative Example 2 cataplasm

| | (% by weight) |
|---|---|
| gelatin | 5.0 |
| sorbitol | 10.0 |
| carboxymethylcellulose | 3.5 |
| glycerol | 25.0 |
| kaolin | 7.0 |
| sodium polyacrylate | 3.0 |
| l-menthol | 0.5 |
| purified water | 46.0 |

The above components were heated and mixed together to thereby obtain a paste. The paste was spread on a foundation, thereby obtaining a cataplasm. The above formulation is the same as in Comparative Example 1 except that the crotamiton as the resolvent for λ-menthol was omitted.

Comparative Example 3 cream

| | (% by weight) |
|---|---|
| liquid paraffin | 10.0 |
| triglyceride of middle-length-chain fatty acid | 5.0 |
| polyethylene glycol monostearate | 3.0 |
| glycerol | 5.0 |
| carboxyvinylpolymer | 1.0 |
| diisopropanolamine | 0.4 |
| methyl p-hydroxybenzoate | 0.2 |
| l-menthol | 2.0 |
| purified water | balance |

The above components were mixed together, thereby obtaining a cream. The above formulation is the same as in Formulation Example 15 except that λ-menthol was employed in place of (1R, 2S, 5R, 8R)-2-(2-methoxy-1-methylethyl)-5-methylcyclohexanol.

Test Example 1

A solution composed of petroleum ether and, dissolved therein, 0.01% of 2-(2-methoxy-1-methylethyl)-5-methylcyclohexanol was applied onto the tip of the tongue and the skin of the inner side of the forearm of each of 10 healthy male adults, and the physiological refrigerating activity thereof was studied. A solution composed of petroleum ether and, dissolved therein, 0.01% of λ-menthol was used as a control. The results are shown in Table 1. The degree of refrigeration was evaluated according to the following criteria:

+++ : very strong refrigeration is felt,
++ : strong refrigeration is felt,
+ : refrigeration is felt, and
− : no refrigeration is felt.

TABLE 1

| | Refrigeration | |
|---|---|---|
| cool feeling sample | top of the tongue | skin of the inner side of the forearm |
| 2-(2-methoxy-1-methylethyl)-5-methylcyclohexanol (Example 2) | +++ | ++ |
| l-menthol | +++ | ++ |

The results of Table 1 demonstrate that 2-(2-methoxy-1-methylethyl)-5-methylcyclohexanol according to the present invention satisfactorily refrigerates not only the tip of the tongue but also the skin as in the use of λ-menthol.

Test Example 2

The cataplasmas obtained in Formulation Examples 8, 17, 18 and 19 and Comparative Example 1 were individually applied onto the skin of the outer side of the forearm of each of 26 healthy male adults, and the physiological refrigerating activities and odors thereof were measured and compared. In particular, the following items were tested and evaluated. The results are shown in Table 2. The evaluation was conducted in such a manner that the test result regarding each of the test items was ranked by the following points and reported by each of the adults under test.

[Test item, classification of test result and points assigned thereto]

| a) | Strength of refrigeration | |
|---|---|---|
| | strong refrigeration | 3 |
| | poor refrigeration | 2 |
| | no refrigeration | 1 |
| b) | Continuity of refrigeration | |
| | more than 3 hr | 3 |
| | from 1 to 3 hr | 2 |
| | less than 1 hr | 1 |
| c) | Immediacy in exertion of refrigeration | |
| | less than 5 min | 3 |
| | from 5 to 10 min | 2 |
| | more than 10 min | 1 |
| d) | Intensity of odor | |
| | powerful odor | 3 |
| | weak odor | 2 |
| | no odor | 1 |

With respect to each of the above four items, the points reported by the 26 adults under test were totaled and averaged. The obtained averages are shown in Table 2.

TABLE 2

| Sample | Test item | | | |
|---|---|---|---|---|
| | Strength of refrigeration | Continuity of refrigeration | Immediacy in exertion of refrigeration | Intensity of odor |
| cataplasm of Formulation Ex. 8 | 2.9 | 2.9 | 2.8 | 1.1 |
| cataplasm of Formulation Ex. 17 | 2.9 | 3.0 | 2.9 | 1.1 |
| cataplasm of Formulation EX. 18 | 2.8 | 3.0 | 2.7 | 1.1 |
| cataplasm of Formulation Ex. 19 | 2.8 | 3.0 | 2.8 | 1.1 |
| cataplasm of Comp. Ex. 1 | 2.9 | 2.5 | 2.5 | 2.9 |

The results of Table 2 demonstrate that the cataplasmas individually containing 2-(2-alkoxy-1-methylethyl)-5-methylcyclohexanols according to the present invention have refrigerating activities equivalent to that of the cataplasm containing λ-menthol, and that neverthless they were practically odorless.

Test Example 3

The cataplasmas obtained in Formulation Examples 8, 18 and 19 and Comparative Example 2 were stored at 5° C., and the changes of crystallization with the lapse of time were observed. The results are shown in Table 3.

TABLE 3

| Sample | Lapse of time | | | | |
|---|---|---|---|---|---|
| | initially | 1 day | 3 days | 7 days | 14 days |
| cataplasm of Formulation Ex. 8 | o | o | o | o | o |
| cataplasm of Formulation EX. 18 | o | o | o | o | o |
| cataplasm of Formulation Ex. 19 | o | o | o | o | o |
| cataplasm of Comp. Ex. 2 | o | o | x | x | x | o: No crystallization is recognized.
x: Crystallization is recognized.

It is apparent from the results of Table 3 that the cataplasmas individually containing the refrigerants according to the present invention were stable over a prolonged period of time even if no resolvent was contained because the 2-(2-alkoxy-1-methylethyl)-5-methylcyclohexanols of the present invention were individually present in the respective bases in the state of being stably dissolved therein, whereas the crystallization of λ-menthol occurred with the lapse of time in the cataplasm of Comparative Example 2 containing λ-menthol as the cool feeling and having no resolvent added thereto.

Test Example 4

The creams of formulation Example 15 and Comparative Example 3 were separately applied in suitable amounts onto the face of each of 20 individuals under test, and the physiological refrigerating activities and odors thereof were measured and compared. In particular, the following items were tested and evaluated. The results are shown in Table 4. The evaluation was conducted in such a manner that the test result regarding each of the test items was ranked by the following 5-level points and reported by each of the individuals under test.

[Test item, classification of test result and points assigned thereto]

| a) | Strength of refrigeration | |
|---|---|---|
| | refrigeration of such a strength as an ache is felt | 5 |
| | strong refrigeration | 4 |
| | appropriate frigeration | 3 |
| | weak but some refrigeration | 2 |
| | no refrigeration | 1 |
| b) | Continuity of refrigeration | |
| | more than 1 hr | 5 |
| | more than 30 min but not more than 1 hr | 4 |
| | more than 10 min but not more than 30 min | 3 |
| | more than 5 min but not more than 10 min | 2 |
| | only initially | 1 |
| c) | Intensity of odor | |
| | odor of such an intensity as the eyes are ached | 5 |
| | powerful odor | 4 |
| | odor recognized | 3 |
| | very weak odor | 2 |
| | no odor | 1 |

With respect to each of the above three items, the points reported by the 20 individuals under test were totaled and averaged. The obtained averages are shown in Table 4.

TABLE 4

| Sample | Test item | | |
|---|---|---|---|
| | Strength of refrigeration | Continuity of refrigeration | Intensity of odor |
| cream of Formulation Ex. 15 | 4.0 | 4.8 | 1.6 |
| cream of Comp. Ex. 3 | 4.2 | 3.5 | 4.7 |

It is apparent from the results of Table 4 that the cream containing (1R, 2S, 5R, 8R)-2-(2-methoxy-1-methylethyl)-5-methylcyclohexanol according to the present invention had a refrigerating activity practically equivalent to that of the cream containing λ-menthol, and that the former was markedly superior to the latter in respect of the continuity of refrigeration and the odor.

Industrial Applicability

The 2-(2-alkoxy-1-methylethyl)-5-methylcyclohexanol of the present invention has such advantageous properties that it satisfactorily refrigerates not only the mouth mucosa but also the skin, is practically odorless as compared with λ-menthol and is stably dissolved in various bases without the need of any resolvent.

Therefore, the cool feeling of the present invention which is capable of satisfactorily refrigerating, for example, the skin practically without being accompanied by peppermint odor and which is excellent in the continuity of refrigeration and the immediacy in exertion of refrigeration can be obtained by the employment of the above cyclohexanol derivative of the present invention.

Moreover, the cool feeling composition of the present invention which is practically odorless and imparts refreshing refrigeration can be obtained by mixing the above cyclohexanol derivative of the present invention into a drug such as an ointment, a cream, a gel, a lotion, a shaping cataplasm, a tape or an internal medicine, a cosmetic such as a powder, a hair tonic, a shampoo or a lip color, a mouth wash such as a dentifrice or a food such as a chewing gum, a candy, an ice or a refreshing drink.

(1R, 2S, 5R, 8R)-2-(2-methoxy-1-methylethyl)-5-methylcyclohexanol which is especially preferred among the cyclohexanol derivatives of the present invention can effectively be produced in pure form from (−)-isopulegol as a starting material by a short process according to the present invention. Therefore, the process of the present invention is extremely advantageous from the industrial viewpoint in the production of the cyclohexanol derivative of the present invention.

The benzyl cyclohexyl ether derivative of the present invention is an intermediate which is extremely useful in the effective production of the cyclohexanol derivative of the present invention according to the above process of the present invention.

What is claimed is:

1. A cyclohexanol derivative represented by the following general formula:

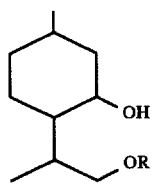

(1)

wherein R represents a linear or branched alkyl group having 1 to 5 carbon atoms.

2. A cool feeling composition comprising the cyclohexanol derivative defined in claim 1.

3. A cyclohexanol derivative represented by the following general formula:

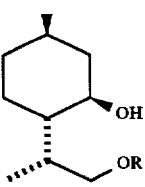

(1a)

wherein R represents a linear or branched alkyl group having 1 to 5 carbon atoms.

4. A process for producing a cyclohexanol derivative represented by the following general formula:

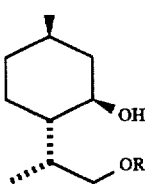

(1a)

wherein R represents a linear or branched alkyl group having 1 to 5 carbon atoms, which comprises reacting (−)-isopulegol represented by the following formula:

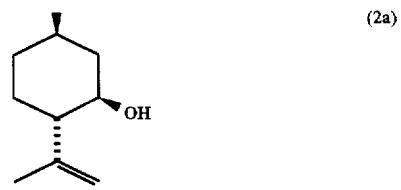

(2a)

with a benzyl halide in the presence of metallic sodium or sodium hydride to thereby form a compound represented by the following formula:

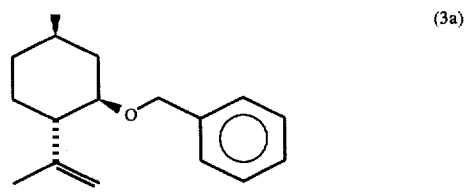

(3a)

hydroborating the compound (3a) to thereby obtain a compound represented by the following formula:

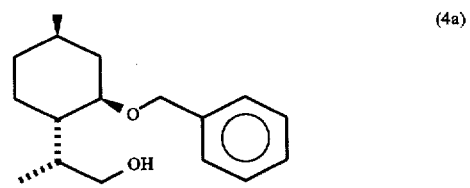

(4a)

alkylating the compound (4a) with an alkylating agent in the presence of a base to thereby form a compound represented by the following general formula:

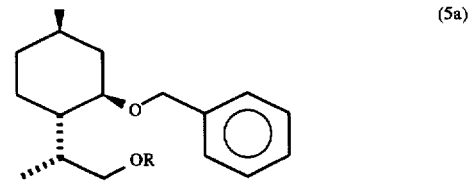

(5a)

wherein R represents a linear or branched alkyl group having 1 to 5 carbon atoms, and catalytically hydrogenating the compound (5a) in the presence of a debenzylating agent.

5. The composition according to claim 2 comprising said cyclohexanol derivative in the amount of 0.001–10% by weight.

6. The cyclohexanol derivative according to claim 3 wherein R is methyl.

7. A cool feeling composition comprising 0.001–10% by weight of a cyclohexanol derivative of formula

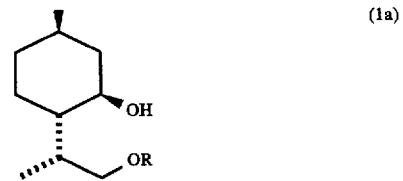

(1a)

wherein R is a linear or branched alkyl group having 1 to 5 carbon atoms.

* * * * *